Figure 1:
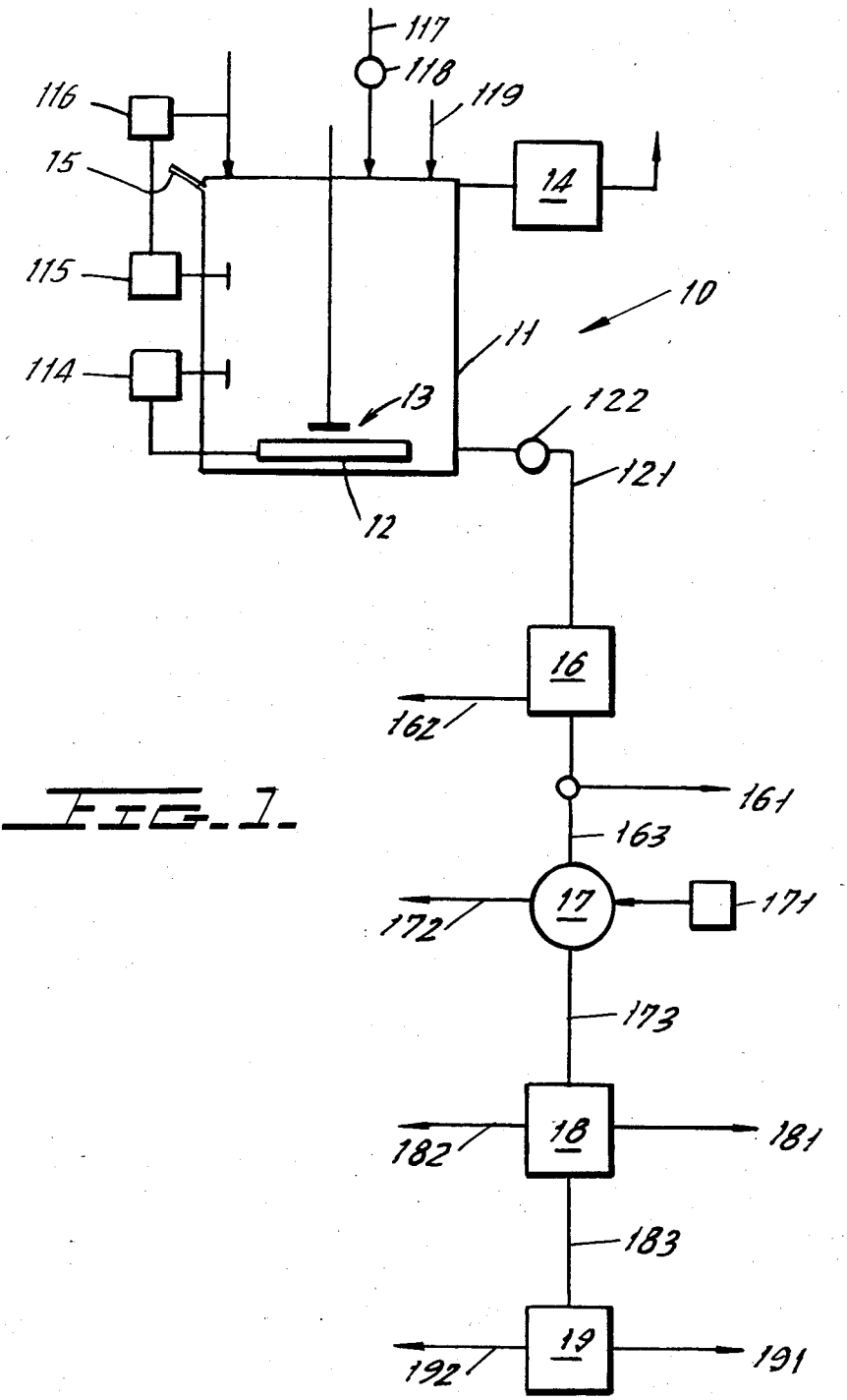

United States Patent [19]

Kaeppeli et al.

[11] Patent Number: 4,628,030
[45] Date of Patent: Dec. 9, 1986

[54] PROCESS FOR THE PRODUCTION OF RHAMNOLIPIDS

[75] Inventors: Othmar Kaeppeli, Würenlos; Luis Guerra-Santos, Zurich, both of Switzerland

[73] Assignee: Petrotec Forschungs AG, Switzerland

[21] Appl. No.: 639,377

[22] Filed: Aug. 9, 1984

[30] Foreign Application Priority Data

Aug. 9, 1983 [CH] Switzerland ............... 4327/83

[51] Int. Cl.$^4$ .................. C12P 19/04; C12R 1/385
[52] U.S. Cl. ................................. 435/101; 435/875
[58] Field of Search ........................... 435/101, 875

[56] References Cited

U.S. PATENT DOCUMENTS 4,286,660  9/1981  Wagner et al. ............... 166/246

FOREIGN PATENT DOCUMENTS 0153634  2/1985  European Pat. Off. .
2150375  4/1972  Fed. Rep. of Germany .
48-43879  5/1973  Japan .
52-54083  5/1977  Japan .

OTHER PUBLICATIONS

Chemical Abstracts; vol. 101 (1984), #128818u; Guerra-Santos, Kaeppeli & Fiechter.
Journal of Antibiotics, vol. 24, No. 12, pp. 855–859; Itoh et al.
Luis Guerra-Santos, Othmar Kappeli and Armin Fiechter, "*Pseudomonas aeruginosa* Biosurfactant Production in Continuous Culture with Glucose as Carbon Source", Applied and Environmental Microbiology, Aug. 1984, pp. 301–305, vol. 48, No. 2.
L. Guerra-Santos, O. Kappeli and A. Fiechter, "Process Development for the Production of Biosurfactants", Third European Congress on Biotechnology, vol. 1, pp. I-506–13.
T. Hirayama and I. Kato, "Novel Methyl Rhamnolipids from *Pseudomonas aeruginosa*", FEBS Letters, vol. 139, No. 1, Mar. 1982.
L. Guerra-Santos, O. Kappeli and A. Fiechter, "Growth and Biosurfactant Production of a Bacteria in Continuous Culture", Proceedings of 1982 International Conference on Microbal Enhancement of Oil Recovery, pp. 12–14.
S. Itoh, H. Honda, F. Tomita and T. Suzuki, "Rhamnolipids Produced by *Pseudonomonas aeruginosa* Grown on n-Parafin (Mixture of $C_{12}$, $C_{13}$ and $C_{14}$ Fractions)", the Journal of Antibiotics, vol. XXIV, No. 12, (1971), pp. 855–859.
K. Hisatsuka, T. Nakahara, N. Sano and K. Yamada, "Formation of Rhamnolipid by *Pseudomonas aeruginosa* and its Function in Hydrocarbon Fermentation", Agr. Biol. Chem., vol. 35, No. 5, pp. 686–692, 1971.
C. Syldatk, S. Lang, U. Matulovic and F. Wagner, "Production of Four Interfacial Active Rhamnolipids from n-Alkanes or Glycerol by Resting Cells of Pseudomonas Species DSM 2874", In: Third Eur. Cong. on Bio-Technol. Proceedings vol. I, Verlag Chemie Weinheim, FRG, pp. 3–8, (1984).
M. M. Burger, L. Glaser and R. M. Burton, "Formation of Rhamnolipids of *Pseudomonas aeruginosa*", J. Biol. Chem. 238:2595–2602 (1963).

(List continued on next page.)

Primary Examiner—Jerome D. Goldberg
Assistant Examiner—Joseph A. Lipovsky
Attorney, Agent, or Firm—Ostrolenk, Faber, Gerb & Soffen

[57] ABSTRACT

For the production of rhamnolipids which can be used as surfactants, microorganism of the genus Pseudomonas are cultivated in a aqueous medium suitable for the growth of the microorganisms under growth conditions; in this process the microorganisms are cultivated in a continuous submerged culture under aerobic conditions, with a continuous supply of fresh culture medium and with continuous removal of a culture solution and microbial cells (biomass); the culture medium has a composition suitable for limiting growth by means of at least two-fold limitation of essential growth substances; a solution of the rhamnolipids produced as metabolite of the microorganisms is separated from the culture broth. For this purpose a continuously operated bioreactor (11) is suitable.

17 Claims, 2 Drawing Figures

OTHER PUBLICATIONS

F. Wagner, U. Behrendt, H. Bock, A. Kretschmer, S. Lang and C. Syldatk, "Production and Chemical Characterization of Surfactants from Rhodococcus Erythropolis and Pseudomonas Sp. Mub Grown on Hydrocarbons", Microbial Enhanced Oil Recovery, Pennwell Bocks, Tulsa, Oklahoma (1983).

D. K. Olsen, H. Janshekar, "Biosurfactant Production and Laboratory Application Tests for Heavy Crude Oil".

F. Wagner, J.-S. Kim, S. Lang, Z.-Y. Li, G. Marwede, U. Matulovic, E. Ristau and C. Syldatk, "Production of Surface Active Anionic Glycolipids by Resting and Immobilized Microbial Cells".

C. Syldatk, S. Lang and F. Wagner, "Chemical and Physical Characterization of Four Interfacial-Active Rhamnolipids from Pseudomonas spec. DSM 2874 Grown on n-Alkanes".

Evans, L. R. and A. Linker, "Production and Characterization of the Slime of *P. aeruginosa*", J. Bacteriol. 116: 915–924 (1973).

Jarvis, F. G. and M. J. Johnson, "A Glycolipid Produced by *P. aeruginosa*", J. Am. Chem. Soc. 71: 4124–4126 (1949).

Goto, S., Murakawa, T. and S. Kuwahara, "Slime Production by *P. aeruginosa II.*, Production by *P. aeruginosa*." J. Microbiol. (Japan) 17: 45–51 (1973).

Hauser, G. and M. L. Karnovsky, "Studies on the Production of Glycolipids by *P. aeruginosa*", J. Bacteriol., 68:645–654 (1954).

PROCESS FOR THE PRODUCTION OF RHAMNOLIPIDS

The invention relates to a microbiological for producing rhamnolipids which exhibit surface activity.

It is known that the microbial growth can be induced when surfactants, i.e. natural or synthetic surface-active agents, are added to their growth media, by virtue of the fact that the surfactants increase the accessibility of the substrate to the microorganisms. Surfactants which are suitable for this purpose can be produced by the microorganisms themselves, or they can be added as adjuvants, e.g in the form of a non-biological surfactant; the surfactants which are produced by the microorganisms themselves are now called biosurfactants, and they can belong to different categories.

Experiments with oil containing oil sludge have shown that microbes can utilize hydrocarbons as a source of carbon and energy. Efforts are being made to use microbes to improve oil recovery, and in this context greater attention has been devoted to biosurfactants which are apparently a significant factor in the biodegradation of hydrocarbons.

From U.S. Pat. Nos. 3,340,930 and 4,096,073, for example, the flooding of mineral oil deposits with an aqueous medium containing surfactants which has been produced by the cultivation of certain microbes which are capable of growing on hydrocarbons from the class of Schizomycetes or yeasts of the genus Saccharomycetes on a culture medium containing hydrocarbons is known. According to U.S. Pat. No. 4,286,660 especially the biosurfactants of glycolipid type which are produced in an aqueous medium with hydrocarbon as a carbon source are suitable for flooding mineral oil deposits; in this case the production can be conducted in bioreactors operating semicontinuously or continously. For example, in continuous operation the work proceeds such that the reactor outflow containing the biosurfactant is injected into the oil reservoir through one well bore, and that it is recovered through a second well bore together with the washed out mineral oil. After separation of the predominately mineral oil portion, the remaining aqueous phase can be returned to the bioreactor and used for the production of glycolipid.

Even though for the production of oil by such methods of "enhanced oil recovery" the usual, synthetic surfactants can be and are being used, because of their adapted or natural occurrence, biosurfactants, such as e.g. the glycolipids, offer special advantages.

Generally, a demand exists for new surfactants and/or improved methods for producing surfactants. A great number of synthetic surfactants are available, but for example with regard to the ratio of effectiveness to biodegradability and/or temperature stability and sensitivity to shear force, or physiological factors, they definitely have room for improvement. Since a multi-purpose synthetic surfactant does not exist, for reasons of i.a. specialization, additional surfactants are necessary.

Therefore, the search for new surfactants goes on, and it would be desirable to implement the biosurfactant production method proposed for oil production techniques for the production of surfactants for other forms of application as well. However, the investigations which have led to the present invention have shown that with conventional cuture media, methods and microorganisms economically feasible production of suitable biosurfactants (e.g. for use as suspension, dispersion and wetting agents or the like for commercial processes or products) cannot be realized at all, or only with great difficulty.

It was found that rhamnolipids of the type described by Itoh, S. et al, J. Antibiot, 24: 855–859, and which can be obtained on n-parrafins by cultivating microorganisms of the genus pseudomonas, especially pseudomonas aerguinosa, would be of advantage as biosurfactants, but according to the state of the art they are only obtainable in batch production by uneconomic methods such as is described e.g. for various Pseudomonas cultures in DE-OS No. 21 50 375.

In addition, the investigations leading to the present invention show that at the present state of the art continuous cultivation does not result in useful products of adequate yield.

It is the objective of the invention to create a process, by means of which rhamnoloipids with a surface activity sufficient for use as surfactants can be produced in a continuous process and with reasonable yields.

This task is solved by the present invention by the creation of a process for the production of rhamnoloipids by cultivating microorganisms of the genus Pseudomonas, especially *Pseudomonas aeruginosa,* in a aqueous culture medium suitable for the growth of such microorganisms under appropriate culture conditions, said process being characterized in that (a) the microorganisms are cultivated in a continuous submerged culture under aerobic conditions and with continuous supply of fresh nutrient medium, as well as continuous removal of a culture broth consisting of partially spent culture medium and produced surfactants, as well as possibly microbial cells (biomass);

(b) the culture medium exhibits a composition suitable for growth limitation by at least double limitation of essential growth substances.

(c) The culture can be used as such for certain areas of application, e.g. for oil recovery, or a solution of the rhamnolipids produced as the metabolite of the microorganisms is separated from the culture medium.

The solution obtained with a rhamnolipid content of typically more than 1 g per liter can be used as such or in concentrated form; if desired the rhamnolipid can be isolated or purified by known methods such as precipitation, and/or affinity chromatography, e.g. with commercially available absorption agents of synthetic polymers such as those based on styrol or aryl acid esters.

From the aforementioned DE-OS No. 21 50 375, it is known that for the production of rhamnolipids by cultivation of microorganisms several species of the genus Pseudomonas can be used, such as *Pseudomonas aeruginosa, Pseudomonas fluorescens, Pseudomonas putida, Pseudomonas cruciviae, Pseudomonas boreopolis, Pseudomonas oleovorans,* and sythetic or natural mutatants of these strains, are capable of producing rhamnolipids; this also applies generally for the process according to the present invention, in which case however the strains of type *Pseudomonas aeruginosa* or its natural or synthetic mutants are preferred.

For the process according to the present invention, various suitable strains of the microorganism of type *Pseudomonas aeruginosa* are known. A new strain of this type is preferably used which is designated Rsan ver, and which was registered with the DSM, Deutsche Sammlung von Mikroorganismen (German Collection of Microorganisms), Grisebachstr. 8, 3400 Goettingen, Federal Republic of Germany, under the registration number DSM 2659 (Rsan ver). The scientific description of the strain is contained in the registration voucher.

When cultivated in suitable media and under suitable conditions *Pseudomonas aeruginose* and especially Rsan ver are capable of producing biosurfactant which significantly lowers the surface tension (ST) and the interfacial tension (IT) of the cell-free culture fluid, e.g. ST of more than 70 $mN.m^{-1}$ to about 30 $mN.m^{-1}$ or less, or IT of more than 25 $mN.m^{-1}$ to 1 $mN.m^{-1}$ or less.

Relating to the present invention it was found that the medium for economic production of biosurfactant with such properties must meet certain conditions, and that the cultivation must take place in a continuous culture ad described below.

Since the microorganisms used in the present invention are Pseudomonas types, with the exception of the special conditions described below to conduct the process according to the present inventions initially the general culture conditions suitable for these microbes can be used (temperature, pH value, essential growth components, trace elements).

For example a temperature range of 20°–40° C. for the cultivation is suitable, and one of 27°–34° C., especially 31°–33° C., is preferred. The pH value of the medium is generally between 4 and 9, preferably between 5 and 7.5, and especially in the range of 6.0 to 6.8. A pH value of about 6.25 is especially advantageous.

With the exception of oxygen which is always present in aerobic cultures, the essential growth components for Pseudomonas strains, including Rsan ver, are carbon, nitrogen, sulfur, phosphorous, sodium, potassium, magnesium and calcium. For the cultivation, the trace elements Fe, Zn, Mn, B, Co, Cu and Mo are also needed.

The aforementioned main and trace elements are as usual needed in assimilatable form and typically in amounts of 1–50 g/l C, 100–2000 mg/l each of N, S, P, Na and K, as well as 10–500 mg/l each of Mg and Ca; the trace elements Zn, Mn, Mo, B, Co and Cu are usually used in amounts of 0.01 to 1 mg/l, and the amount of iron can be varied between trace portions and such of 100 mg/l. As described further below, according to the present invention certain limitations are required.

As a source for the growth components, including trace elements, the substances usual for this purpose, e.g. nitrates, ammonium salts, sulfates, phosphates, haloid salts or corresponding bases or acids can be used. The selection of the carbon source in not critical insofar as according to the present invention not only hydrocarbons, but also carbohydrates, are suitable, and as the latter are frequently more advantageous; homogeneous aqueous media, and correspondingly water-soluble carbohydrates such as sugar are preferably used. Glucose is a preferred example for the carbon source.

To conduct the process according to the present invention continuous aerobic submerged conditions are used, i.e. generally in an almost constant culture volume to which fresh culture medium is continuously added and from which culture broth, i.e. a mixture of biomass and a culture supernatant containing the spent medium and the extra-cellular metabolites, is removed.

When expressed as a fraction of the constant volume introduced into the reactor per time unit, the medium input, which in continuous production is equal to the outflow rate, constitutes the dilution rate. A dilution rate of e.g. 0.1. $h^{-1}$ means that per hour 10% of the constant culture volume is replaced by fresh medium, e.g. 1 liter of medium per hour in a reactor with a working volume of 10 liters.

In this context, it was established that dilution rates of higher than 0.3. $h^{-1}$ lead to a significant decrease in the biosurfactant production, and that the highest biosurfactant productivity is usually achieved by the process according to the present invention at dilution rates below 0.2. $h^{-1}$. Consequently, dilution rates of less than 0.3 $h^{-1}$, and especially less than 0.2. $h^{-1}$, are preferred.

Since the target product of the process according to the present invention is extra-cellular biosurfactant, the biomass constitutes a side product; it is hence generally advantageous for the biosurfactant portion of the culture broth to be kept as large and the biomass portion as small as possible.

With this objective in mind, it was established that the relationship of biosurfactant to biomass portion can be increased by limiting the growth of the microorganisms at least two-fold, i.e. by means of the culture medium containing only limited amounts of two or more essential growth substances.

A growth substance in the culture medium is designated as being limited when its reduction in the growth medium leads to a noticable reduction in the biomass production.

When producing with a continuous culture, this limitation can be established by significantly reduced amounts of the limiting growth substance or substances being present in the residual medium. Here, a portion is regarded as being "significantly reduced" when the spent medium contains less than half of the limiting growth substance, and normally has dropped to less than 1% of the normal amount of the fresh medium. In the preferred case, a limiting growth substance in the spent medium cannot be established with the normal production monitoring methods.

The direct consequence of the foregoing is that the degree of limitation can vary within certain limits. Generally, according to the present invention a pronounced limitation, i.e. a reduction of the content of limiting growth factor in the spent medium by 99% and preferably below the verification limit, is preferred.

Limitation of the nitrogen and the iron and/or magnesium of the fresh culture medium is preferred. A limitation by phosphorous is less advantageous; here, a certain surplus can even be expedient. A C/P ratio of less than 16 is generally preferred. The limitation by C lies within the scope of the invention. Limitation by Na, K, Cl and other trace elements than iron is not preferred. The C/N ratio is preferably between 8 and 30, especially between 11 and 22, preferably at about 18. In other words this means that the amount of C in the fresh medium is preferably 8–30 times, or 11–22 times, and e.g. 18 times larger than the amount of N by weight; in this case nitrates are frequently preferred over ammonium salts as a source of nitrogen.

In addition, with the process according to the present invention the C/Fe ratio usually exceeds 1500, preferably 3000 and is typically between 3000 and 80,000. Especially good results are obtained e.g. with 27.5 μg $FeSO_4.7H_2O$ per gram glucose (C source). Since these preferred Fe portions are relatively very low, the use of complex additives such as yeast extract and other more or less natural mixtures which contain different and correspondingly poorly determinable portions of essential growth substances is less expedient. For the invention minimal media, i.e. sythetic culture media with relatively exactly defined composition, are generally preferred.

The culture broth continuously removed from the continuous culture according to the present invention is a mixture of spent medium and biomass; this mixture contains the metabolically produced biosurfactant which is normally a rhamnoside or a rhamnolipid. The lipid portion of the glycolipid produced by the process according to the invention is not regarded as critical.

The rhamnoside, which in the process according to the present invention can typically be obtained in portions of from 0.5 to 2 g/l is normally dissolved in the culture solution, namely predominantly in the culture supernatant. Correspondingly, the rhamnoside solution is separated from the biomass, e.g. by centrifuging or filtrating, and in this form it can be used for a specific surfactant application, e.g. for enhancement of oil recovery.

For other purposes, e.g. as a suspension, dispersing, emulsifying or wetting agent for typical technical processes and/or commercial products the biosurfactant can be isolated by precipitation and/or extraction from the culture supernatant. For precipitation, agents such as zinc chloride or calcium chloride can be used. For the extraction, organic solvents such as diethylether, chloroform and ethylacetate can be used. In addition a raw product can be obtained by precipitation, this product can in turn—possibly as a suspension in a buffer medium—be extracted with organic solvents. From the extract, almost pure biosurfactant can be obtained by evaporation of the solvent; within certain limits the pH value can be used to influence precipitation.

From the biomass, further biosurfactants or biosurfactant solutions can be obtained, possibly after treatment to destroy the cell walls, and used or processed in a manner as described above.

The drawings serve for further explanation of the invention on the basis of an example of an embodiment. Shown are:

FIG. 1 The diagram of the execution of an embodiment of the process, and

Figure 2:
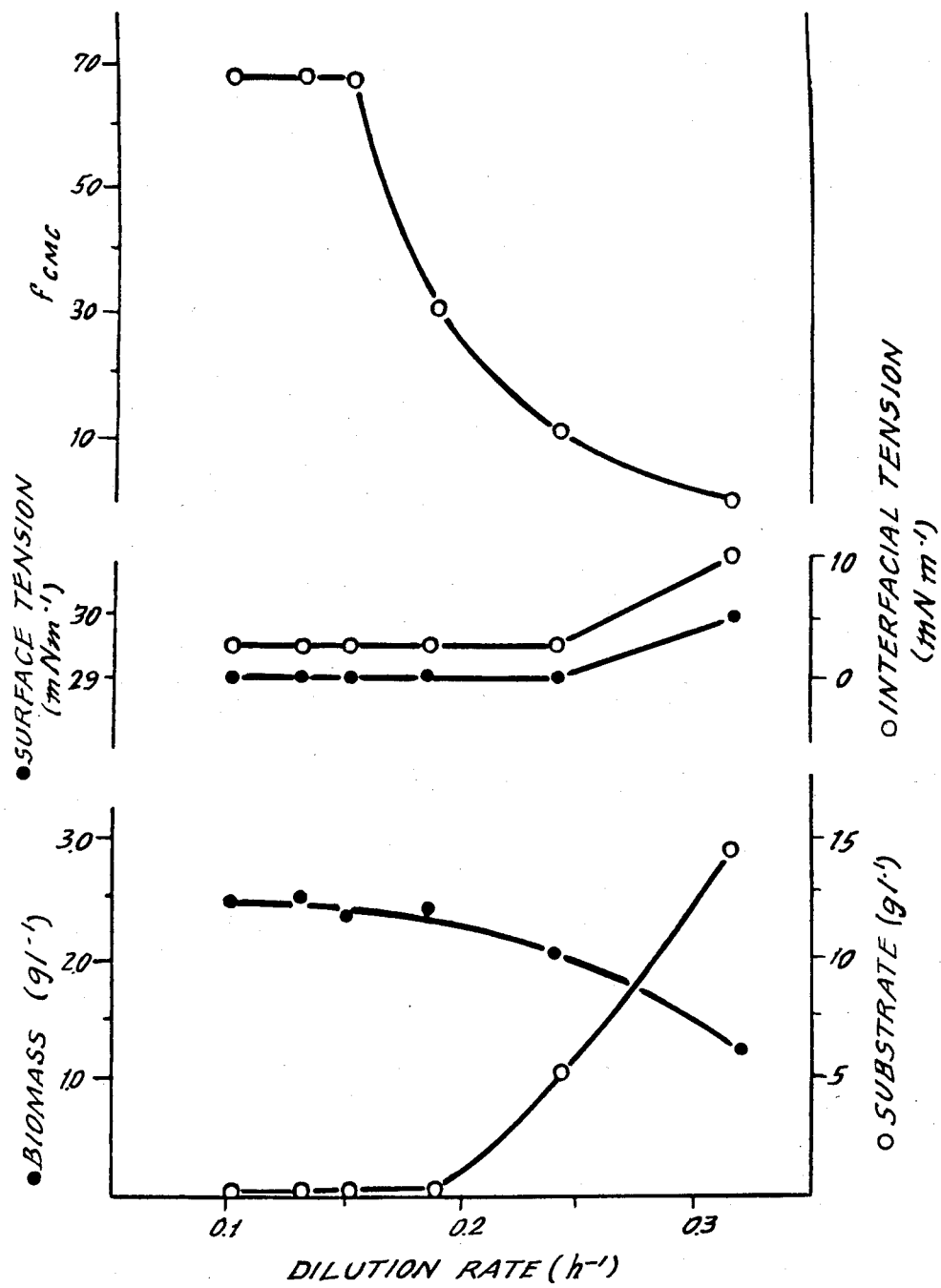

FIG. 2 The productivity/dilution rate relationship in the execution of the process.

To conduct the process shown schematically in FIG. 1, a bioreactor 11 is used for the cultivation step 10, said reactor being furnished with a heater 12, a turbine-driven stirrer 13 and a foam breaker 14. The line 15 can be used for inoculating into the initially charged nutrient solution for starting up the cultivation process and for sampling.

The heater 12 is controlled with the temperature controller 114 to keep the temperature of the reactor contents at an almost constant value. The pH value is continuously monitored by the meter 115, and possibly held at the setpoint with the aid of a controlled acid-/base feed device 116. Fresh culture medium is fed into the reactor 11 through the feed line 117. The medium feed rate can be controlled with the feed pump 118. In addition oxygen, air or another oxygen-containing gas mixture is fed through the line 119 in an amount sufficient to uphold aerobic conditions.

In continuous cultivation, culture broth is removed via the line 121; the medium outflow rate can be adjusted with the pump 122.

In addition, equipment (not shown) is foreseen to sterilize the reactor and to measure further parameters such as oxygen content.

EXAMPLE

For the initiation of the process a previously sterilized 5-liter reactor 11 was filled for continuous operation with frish, sterile culture medium with the composition given in the following table.

TABLE I

| Component | Concentration (liter) |
| --- | --- |
| Glucose | 18.2 g |
| $NaNO_3$ | 2.5 g |
| $MgSO_4.7H_2O$ | 0.2 g |
| KCl | 0.1 g |
| NaCl | 0.1 g |
| $H_3PO_4$ (85%) | 1.0 ml |
| $CaCl_2.2H_2O$ | 50 mg |
| $FeSO_4.7H_2O$ | 0.5 mg |
| $ZnSO_4.7H_2O$ | 1.5 mg |
| $MnSO_4.2H_2O$ | 1.5 mg |
| $H_3BO_3$ | 0.3 mg |
| $CuSO_4.5H_2O$ | 0.15 mg |
| $CoCl_2.6H_2O$ | 0.15 mg |
| $Na_2MoO_4.2H_2O$ | 0.10 mg |
| demineralized water | rest |

After the stirrer is turned on (1500 rpm), the temperature of the medium was brought up to 37° C. and held at this value by the temperature controller 114. The pH value was adjusted to 6.5 with one normal solution of KOH and monitored by the measuring device 115. The reactor working volume was 1.5 liter. The reactor was inoculated with 250-300 ml inoculum of Rsan ver (DSM 2659), operated for 8 hours at constant temperature and supplied with fresh air through the aeration line at the rate of 2.25 liters/minute. The air left the reactor through the discharge line via the foam breaker 14 (operated at 2000 rpm).

When the startup time was terminated, under otherwise identical conditions the pump 122 was started to obtain a culture outflow rate of 150 ml per hour. At the same time the pump 118 in the supply line 117 was started to allow 150 ml of fresh culture medium to flow into the reactor 11 per hour.

In the first separation stage 16, e.g. a centrifuge or a filter, the culture was separated into biomass and cell-free culture solution. The biomass is removed via line 162 and possibly aftertreated or utilized.

The cell-free culture solution containing biosurfactant can be removed either via 161 for direct utilization in this form or led via 163 into a second separation stage 17, and separated there from the rest of the solution through precipitation by the addition of precipitants from 171 or through extraction by adding solvents from 171, the rest of the solution which is free of biosurfactant being removed via 172 and which can, if desired, be processed for the production of fresh culture medium.

The precipitate separated in the separation stage 17 or the extract which has been taken from there can be transferred via 173 into a first purification stage 18, and depending on the type of the raw material obtained in stage 17, resuspended and extracted, or freed from the solvent. Accordingly, in the purification stage 18 either a purified biosurfactant product can be obtained and removed via 181, or transferred via 183 into a second purification stage 19 and recovered there via 191. The residues of the respective purification stages are removed via 182 or 192.

Continuous measurement of the composition of the spent nutrient medium removed through the line 121 shows that the C, N and Fe of the medium are limited, in that portions of these growth substances could almost no longer be established in the spent medium.

The biosurfactant was obtained in a yield corresponding to about 80 mg of rhamnose per gram of substrate carbon, corresponding to a rhamnoside portion of the spent medium of 640 mg/liter, or a surfactant portion of 1–1.5 g/liter.

The surface tension (ST) of the biosurfactant solution flowing off through the line 121 was less than 30 (mN.m$^{-1}$), the interfacial tension (IT) below 1 (mN.m$^{-1}$), determined at room temperature (20° C.) according to the usual ring method and with a modified Dunuoy tensiometer as is available from Messrs. Fisher, USA, under the desination "Auto-Tensiomat".

Biologically, the biosurfactant obtained is easily degradable and can be used to advantage especially where physiologically absolutely safe surfactants are needed, e.g. in the food industry or in the manufacture of physiologically absolutely safe products.

The excellent effectiveness of biosurfactant solutions for enhanced oil recovery can be recognized, for example, by the fact that with a concentration of 0.3 g/100 ml the biosurfactant solution exhibits an at least equivalent oil flushing effect (33% residual oil recovery) as a non-biological surfactant (PYRONATE 40, a petroleum sulfonate available from Messrs. Witco Co., USA) which is commercially available for this application in a ten times higher concentration (3 g/100 m.; 31% residual oil recovery), namely when being evaluated in the "Sandpack Flooding Test".

With the productivity dilution rate characteristic shown in FIG. 2 the dilution rate used in various production runs is plotted on the abcissa with the dimension [h$^{-1}$]. In the bottom part the ordinate on the left shows the biomass obtained (in grams per liter), in the middle part the surface tension of the culture broth (in millinewton per meter) and in the top part the factor f derived from the critical micel concentration (CMC) which serves to evaluate the biosurfactant concentration.

In the lower part, the right ordinate shows the substrate concentration (in grams per liter), and in the middle part the interface tension (in millinewton per meter).

From FIG. 2, it can be seen that with dilution rates of below 0.3, and especially below 0.2, better results with regard to surfactant properties and surfactant yield can be achieved.

We claim:

1. In a process for producing rhamnolipids usable as surfactants by the cultivation of rhamnolipid producing microorganisms of the genus Pseudomonas in an aqueous culture medium suitable for the growth of said microorganisms, the improvement which comprises
    (a) culturing said microorganisms in a continuous submerged culture under aerobic conditions and with a continuous supply of fresh culture medium, and continuous removal of a solution of partially spent culture medium and produced surfactants, at a dilution rate of below 0.3 h$^{-1}$ and
    (b) limiting the amount of at least two essential growth substances selected from the group consisting of carbon, nitrogen, sulfur, phosphorous, sodium, potassium, magnesium, calcium, iron, zinc, manganese, boron, cobalt, copper and molybdenum, in the culture medium such that the quantity of essential growth substance in the partially spent culture medium is less than half of the amount in the fresh culture medium.

2. Process as claimed in claim 1, wherein Pseudomonas microorganisms of the type *Pseudomonas aeruginosa* are used.

3. Process as claimed in claim 2, wherein *Pseudomonas aeruginosa* of the strain DSM 2659 (Rsan ver) are used.

4. Process as claimed in any one of claims 1, 2 and 3, wherein the nitrogen portion of the culture medium is limited.

5. Process as claimed in claim 1, wherein the iron portion of the culture medium is limited.

6. Process as claimed in claim 1, wherein the magnesium portion of the culture medium is limited.

7. Process as claimed in claim 1, wherein production is conducted with a dilution rate of below 0.2 h$^{-1}$.

8. Process as claimed in claim 1, wherein a solution of the rhamnolipids produced as metabolite of the microorganism is separated from the culture broth.

9. Process as claimed in claim 8, wherein the solution obtained is processed for isolation of the rhamnolipid by precipitation or affinity chromatography.

10. Process as claimed in claim 1, wherein the carbon source for the growth of the microorganisms in the culture medium comprises water-soluble carbohydrate.

11. Process as claimed in claim 10, wherein the carbohydrate is glucose.

12. Process as claimed in claim 1, wherein the phosphorous portion of the culture medium is not limited.

13. Process as claimed in claim 1, wherein the carbon/phosphorous ratio in the culture medium is less than 16.

14. Process as claimed in claim 1, wherein the carbon/nitrogen ratio in the culture medium is between 8 and 30.

15. Process as claimed in claim 14, wherein the carbon/nitrogen ratio in the culture medium is about 18.

16. Process as claimed in claim 1, wherein the components to the extent not limiting are 1–50 g/l C, 100–2000 mg/l of each of N, S, P, Na and K, 10–500 mg/l of each of Mg and Ca, 0.01–1 mg/l of each of Zn, Mn, Mo, B, Co and Cu, and up to 100 mg/l Fe; the ratio C/P is less than 16; C/N is 8–30; C/Fe is more than 1500; and the microorganism is *Pseudomonas aeruginosa*.

17. Process as claimed in claim 16, wherein C/N is 11–22 and C/Fe is more than 3000; the dilution rate is less than 0.2$^{-h}$; and the microorganism is strain DSM 2569 (Rsan ver).

* * * * *